(12) United States Patent  
Bick et al.

(10) Patent No.: US 9,406,489 B2
(45) Date of Patent: Aug. 2, 2016

(54) INVESTIGATING CHEMICAL-BASED EVENTS THAT OCCUR IN VEHICLES

(71) Applicant: The Boeing Company, Chicago, IL (US)

(72) Inventors: Cheryl E. Bick, Redmond, WA (US); Joe M. Baratto, Seattle, WA (US)

(73) Assignee: THE BOEING COMPANY, Chicago, IL (US)

(*) Notice: Subject to any disclaimer, the term of this patent is extended or adjusted under 35 U.S.C. 154(b) by 0 days.

(21) Appl. No.: 14/496,126

(22) Filed: Sep. 25, 2014

(65) Prior Publication Data
US 2016/0093481 A1    Mar. 31, 2016

(51) Int. Cl.
H01J 49/00    (2006.01)
H01J 49/26    (2006.01)
G01N 30/00    (2006.01)

(52) U.S. Cl.
CPC ............ H01J 49/0031 (2013.01); G01N 30/00 (2013.01); H01J 49/0022 (2013.01); H01J 49/26 (2013.01)

(58) Field of Classification Search
USPC ........................................................ 250/282
See application file for complete search history.

(56) References Cited

U.S. PATENT DOCUMENTS

| | | | | |
|---|---|---|---|---|
| 5,877,035 A * | 3/1999 | Fujino | .................... | G01N 21/94 257/E21.525 |
| 6,788,407 B1 * | 9/2004 | Higdon | .................. | G01N 21/65 356/301 |
| 7,223,970 B2 * | 5/2007 | Miller | ...................... | F03H 1/00 250/281 |
| 7,383,129 B1 * | 6/2008 | Baillot | .................. | G01N 21/94 702/19 |
| 8,592,751 B2 * | 11/2013 | Miller | .................. | G01N 27/624 250/282 |

OTHER PUBLICATIONS

Barrato et al., "Gas Sampling System," U.S. Appl. No. 13/592,965, filed Aug. 23, 2012, 55 pages.
"HAPSITE Smart Plus: Chemical Identification System," INFICON, Specification Brochure, copyright 2008, 2 pages.

* cited by examiner

*Primary Examiner* — Phillip A Johnston
(74) *Attorney, Agent, or Firm* — Yee & Associates, P.C.

(57) ABSTRACT

A method and apparatus for investigating a chemical-based event inside a vehicle without significant delay. A number of samples of air are collected at a number of locations inside the vehicle in response to a detection of the chemical-based event inside the vehicle. A number of chemical profiles for the number of samples are generated on-site using a portable chemical profiling device. A probable cause of the chemical-based event is identified using at least one of the number of chemical profiles.

20 Claims, 10 Drawing Sheets

INVESTIGATING CHEMICAL-BASED EVENTS THAT OCCUR IN VEHICLES

BACKGROUND INFORMATION

1. Field

The present disclosure relates generally to vehicles and, in particular, to chemical-based events, such as odors, that are detected in vehicles. Still more particularly, the present disclosure relates to a method, apparatus, and system for rapidly investigating these types of chemical-based events that occur in vehicles, such as aircraft, to determine the causes of these events in the vehicles.

2. Background

Within a vehicle, multiple systems may be working both independently and together to ensure that the vehicle operates within selected tolerances. In some situations, an event may occur that affects operation of the vehicle in an undesirable manner. Depending on the type of event, the first detectable sign of the event may be an odor within the vehicle or a physical reaction by one or persons onboard the vehicle. It may be important to be able to quickly identify the event that caused the odor or physical reaction. For example, if the cause of the odor or physical reaction is an issue with a particular part or system in the vehicle, identifying this cause quickly may allow the part or system to be more quickly repaired or replaced as needed.

As one example, the vehicle may take the form of an aircraft. During flight, an event that occurs within an environmental system of the aircraft may cause an odor to be detected by a passenger or crew member. This odor may be caused by changes in the air inside the aircraft resulting from the event that occurs within the environmental system. The changes in the aircraft may include, for example, without limitation, an introduction of one or more chemical compounds into the air inside the aircraft, a change in the proportional concentrations of one or more chemical compounds in the air inside the aircraft, or some combination thereof.

Analysis of the one or more chemical compounds causing the odor detected may provide an indication of the type of event that has occurred. However, with some currently available systems, identifying the one or more chemical compounds that are causing the odor may be more difficult, time-consuming, and in some cases, more expensive than desired. With currently available methods and systems for identifying the chemical compounds causing the odor, investigation of the odor may not be able to be performed until several hours or even days after the initial detection of the odor. In situations where the odor is intermittent, the delayed identification may hamper identifying the cause of the odor and the location of this cause.

Currently available systems may be unable to (1) rapidly identify the one or more chemical compounds causing a chemical-based event that occurs inside a vehicle; (2) link these chemical compounds to the chemical-based event; (3) and link these chemical compounds to the cause of the event, while still onboard the vehicle. As one example, currently available systems may require that samples of air from inside an aircraft be taken to a laboratory for analysis. Typically, the laboratory is located remotely relative to the location of the aircraft. For example, the laboratory may be located away from the runway or airport gate at which the aircraft is located, many miles from the airport at which the aircraft is located, or in a different city or state.

Consequently, the overall process involved in identifying the chemical compounds causing the odor and linking these chemical compounds to the event that caused the odor may take days or weeks, thereby reducing the likelihood of detecting the cause of the odor. Therefore, it would be desirable to have a method and apparatus that take into account at least some of the issues discussed above, as well as other possible issues.

SUMMARY

In one illustrative embodiment, a method for investigating a chemical-based event inside a vehicle without significant delay is provided. A number of samples of air are collected at a number of locations inside the vehicle in response to a detection of the chemical-based event inside the vehicle. A number of chemical profiles for the number of samples are generated on-site using a portable chemical profiling device. A probable cause of the chemical-based event is identified using at least one of the number of chemical profiles.

In another illustrative embodiment, a method for investigating a chemical-based event inside an aircraft without significant delay is provided. A number of samples of air are collected at a number of locations inside the aircraft in response to a detection of the chemical-based event inside the aircraft. A number of chemical profiles for the number of samples are generated on-site using a portable chemical profiling device. A probable cause of the chemical-based event is identified using at least one of the number of chemical profiles.

In another illustrative embodiment, a chemical investigation system comprises a portable chemical profiling device, a database, and a cause identification system. The portable chemical profiling device collects a number of samples of air at a number of locations inside a vehicle in response to a detection of a chemical-based event inside the vehicle. The portable chemical profiling device generates a number of chemical profiles for the number of samples on-site using the portable chemical profiling device. The database stores a plurality of reference chemical profiles associated with a plurality of known causes of chemical-based events in the vehicle. The cause identification system identifies a probable cause of the chemical-based event using at least one of the number of chemical profiles.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

DETAILED DESCRIPTION

Figure 1:
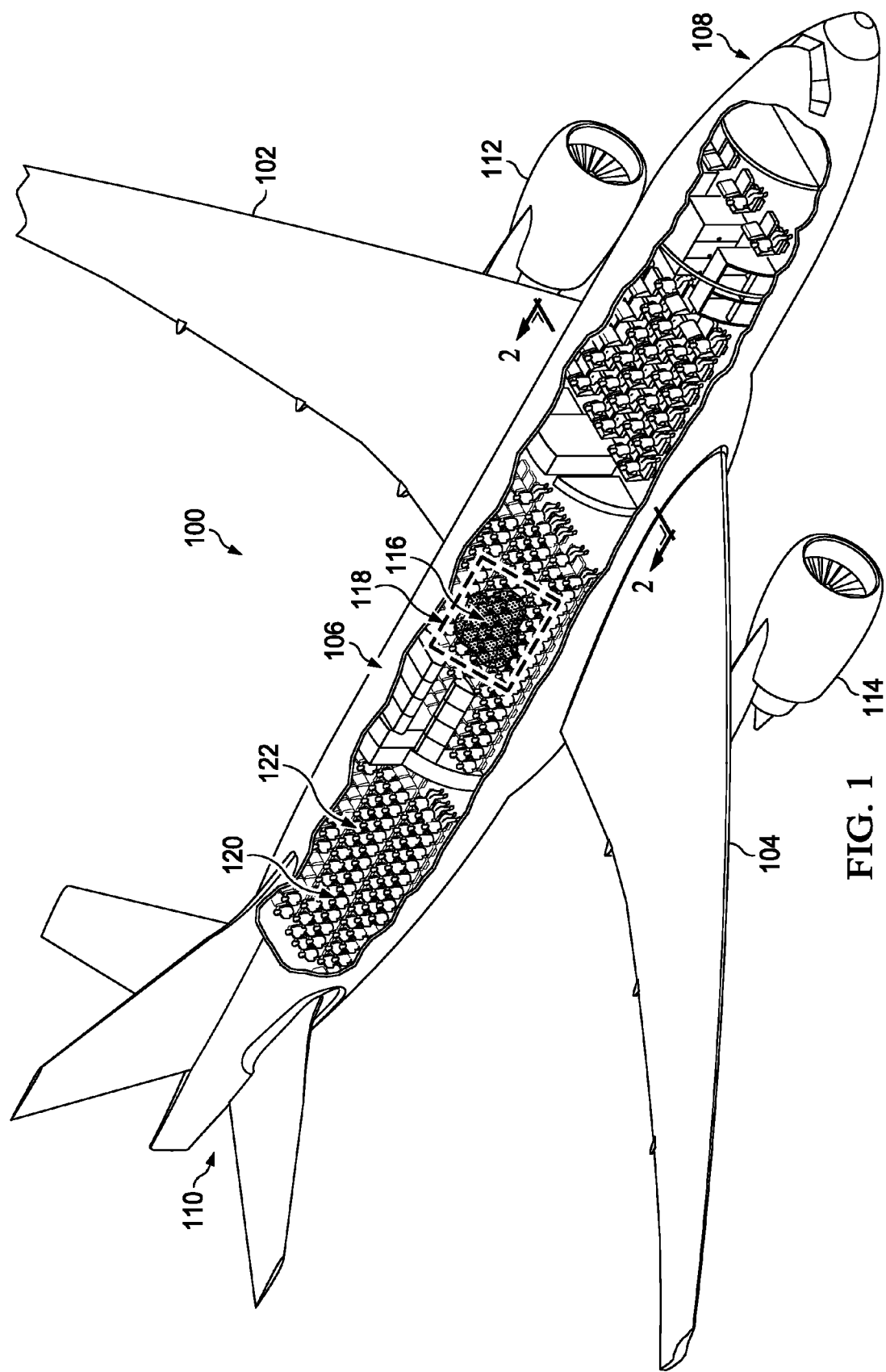
FIG. 1 is an illustration of an isometric view of an aircraft having an exposed fuselage in accordance with an illustrative embodiment.

The illustrative embodiments recognize and take into account different considerations. For example, the illustrative embodiments recognize and take into account that it may be desirable to investigate an odor that is detected inside a vehicle, such as an aircraft, and determine the cause of that odor without having to leave the vehicle or take samples of air from inside the vehicle to a remotely located laboratory. In particular, the illustrative embodiments recognize and take into account that it may be desirable to have the capability to investigate an odor that is detected inside the vehicle by sampling the air inside the vehicle, analyzing these samples while still onboard the vehicle, and determining the cause of the odor while still onboard the vehicle.

Further, the illustrative embodiments recognize and take into account that, in some cases, when the odor is detected inside a vehicle, such as an aircraft, during flight of the aircraft, it may be desirable to investigate the odor during flight prior to landing. Depending on the cause of the odor, this type of early investigation may enable crew members to quickly locate the cause of the odor, perform the operations needed to manage the odor, restore air quality, perform repairs, or perform some combination thereof, as needed. When the aircraft is a passenger aircraft, this type of early investigation and management may improve the overall experience, and in some cases safety, of the passengers onboard the aircraft for the remainder of their flight, and otherwise prevent disturbances during the flight.

The illustrative embodiments also recognize and take into account that the transportation of certain types of cargo may require that certain systems onboard an aircraft operate in a certain manner. For example, the transportation of certain types of cargo may require that a selected environmental state be maintained within a particular portion or enclosed area within the aircraft. This selected environmental state may include, for example, without limitation, a particular air temperature or range of temperatures, a particular air content, or some other type of property.

In one example, an event occurring within the environmental system maintaining this environmental state may cause an odor to be detected or a physical reaction to be experienced by a crew member or passenger of the aircraft prior to takeoff, during flight, or after landing. Early investigation and management of the odor or physical reaction, without significant delay, may help, for example, the crew members identify any undesired deviations from the selected environmental state and manage the environmental system to help manage the selected environmental state.

Additionally, the illustrative embodiments recognize and take into account that it may be desirable to have a capability of investigating a chemical-based event, such as the detection of an odor, onboard a vehicle during any stage in the lifecycle of the vehicle in a manner that provides immediate or near-immediate results. In other words, the results may be provided without significant delay. As one illustrative example, during certification of an aircraft, testing of the aircraft pre-service, testing of the aircraft in-service, or other operations, being able to investigate a chemical-based event that occurs during one of these operations and identify the cause of the chemical-based event on-site may reduce and, in some cases, eliminate the need for further off-site investigation or laboratory testing. Consequently, this type of investigation may enable these operations to continue to be performed without significant delay.

Thus, the illustrative embodiments provide a method, apparatus, and system for investigating a chemical-based event, such as an odor, inside a vehicle. In one illustrative example, a number of samples of air may be collected at a number of locations inside the vehicle in response to a detection of the chemical-based event inside the vehicle. A number of chemical profiles for the number of samples may be generated on-site using a portable chemical profiling device. For example, when the vehicle is an aircraft, both the collection of the samples and the generation of the chemical profiles for the samples may be performed onboard the aircraft. Thereafter, a probable cause of the chemical-based event may be identified using at least one of the number of chemical profiles generated. Depending on the implementation, the identification of this probable cause may also be performed on-site.

In this manner, a chemical-based event, such as the detection of an odor or an experiencing of a physical reaction by a person onboard the aircraft, may be investigated substantially completely while onboard the aircraft. The type of investigation process provided by the illustrative embodiments may reduce the overall time, expense, and effort associated with investigating these types of chemical-based events. The illustrative embodiments provide a technical solution to the problem of how to quickly, accurately, and easily investigate and identify the cause of a chemical-based event that occurs inside an aircraft.

Referring now to the figures and, in particular, with reference to FIG. 1, an illustration of an isometric view of an aircraft having an exposed fuselage is depicted in accordance with an illustrative embodiment. In this illustrative example, aircraft 100 may be an example of a vehicle in which a chemical-based event has occurred.

As depicted, aircraft 100 may include wing 102, wing 104, fuselage 106, nose portion 108, and tail portion 110. Engine system 112 and engine system 114 may be attached to wing 102 and wing 104, respectively. A chemical-based event, such as chemical-based event 116, may occur in response to an event related to any one or more of the components or systems in wing 102, wing 104, fuselage 106, nose portion 108, tail portion 110, engine system 112, engine system 114, or combination thereof.

For example, during flight, chemical-based event 116 may occur within passenger cabin 120, which is located inside fuselage 106 of aircraft 100. Chemical-based event 116 may occur most strongly within area 118 inside passenger cabin 120. In one illustrative example, chemical-based event 116 may be the detection of an odor within passenger cabin 120 by one or more of passengers 122 during fight of aircraft 100. The odor may be most strongly detected within area 118.

In another illustrative example, chemical-based event 116 may be a physical reaction experienced by one or more passengers during the flight of aircraft 100. The physical reaction may take the form of, for example, without limitation, watery eyes, a headache, a skin-related symptom, or some other type of physical reaction. In other illustrative examples, chemical-based event 116 may include the detection of multiple physical reactions.

The cause of chemical-based event 116 may be unknown. Further, the location of that cause may be unknown. A portable chemical profiling device, such as portable chemical profiling device 200 in FIG. 2 described below, may be used to investigate chemical-based event 116.

Figure 2:
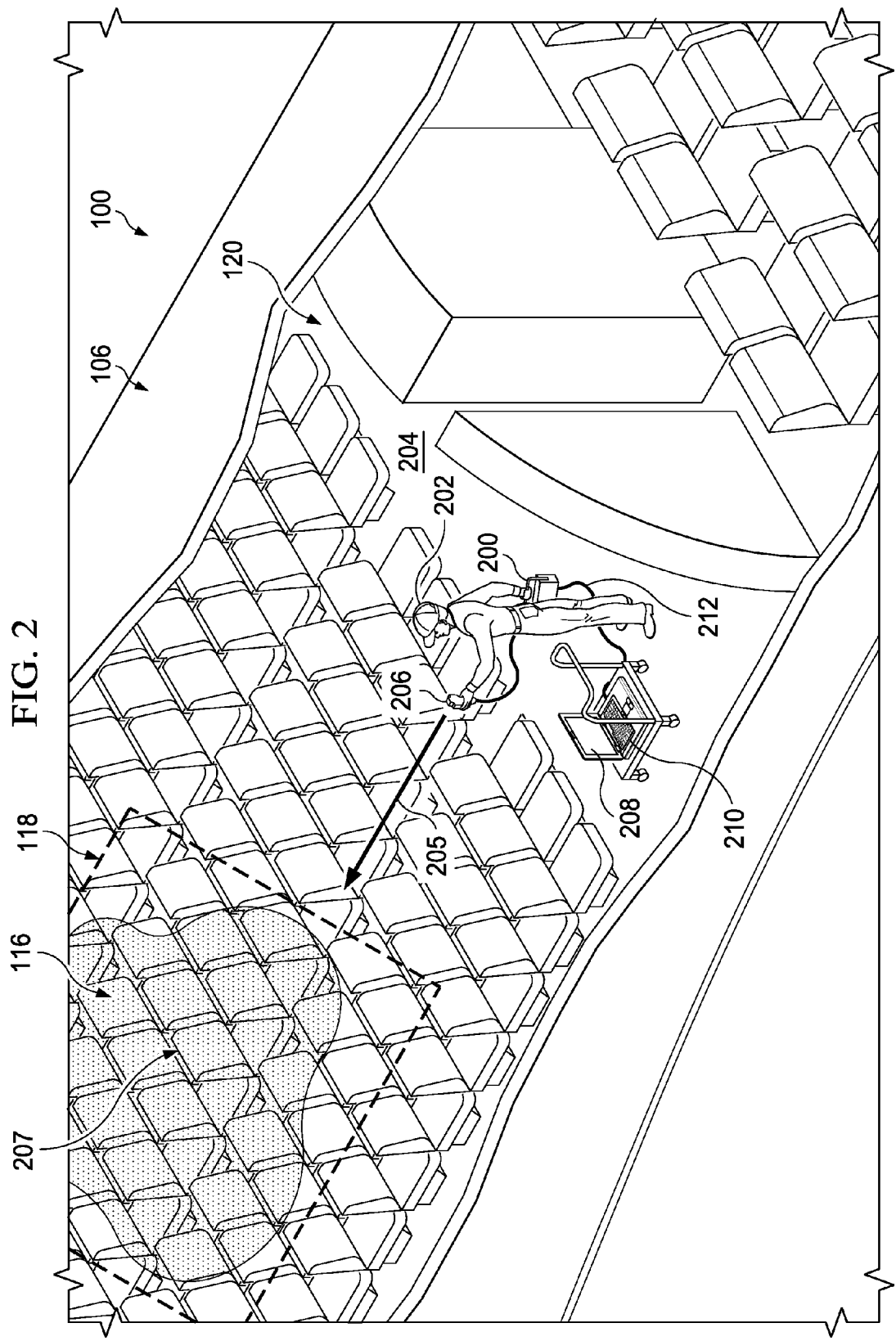
FIG. 2 is an illustration of an enlarged view of an area inside an aircraft in accordance with an illustrative embodiment.

Turning now to FIG. 2, an illustration of an enlarged view of area 118 from FIG. 1 is depicted in accordance with an illustrative embodiment. As depicted, portable chemical profiling device 200 may be used to investigate chemical-based event 116 inside area 118.

Portable chemical profiling device 200 has sampling element 206. Investigator 202 may use sampling element 206 of portable chemical profiling device 200 to take samples of air 204 inside passenger cabin 120. Investigator 202 may be a technician, an engineer, a mechanic, a crew member, or some other type of human operator.

In this illustrative example, investigator 202 may move in the direction of arrow 205 towards area 118 where chemical-based event 116 is strongest to take samples of air 204 within area 118. Any number of samples may be taken. For example, one sample, two samples, ten samples, twenty samples, forty samples, or some other number of samples may be taken.

In some situations, it may be desirable to have a non-human perform the investigation of chemical-based event 116. Thus, although investigator 202 is depicted as a human being in this illustrative example, investigator 202 may take the form of a robotic operator in other examples. For example, investigator 202 may be a robotic vehicle having a robotic arm used to hold sampling element 206.

Portable chemical profiling device 200 may generate a chemical profile for each of the samples collected without significant delay. For example, portable chemical profiling device 200 may generate a chemical profile for each sample collected within seconds or minutes of obtaining the sample. In this illustrative example, portable chemical profiling device 200 may have a sensitivity of at least a parts-per-billion sensitivity. Each of the samples collected using sampling element 206 may have a volume sufficient to identify a number of chemical compounds in the sample based on the corresponding chemical profile generated. The chemical profiles generated by portable chemical profiling device 200 may be used by cause identification system 208 to identify a probable cause of chemical-based event 116.

In this illustrative example, cause identification system 208 is implemented on laptop computer 210. Laptop computer 210 may be configured for the special purpose of identifying the probable causes of chemical-based events based off of chemical profiles generated by portable chemical profiling device 200. Although laptop computer 210 is depicted in FIG. 2 as being used with portable chemical profiling device 200, cause identification system 208 on laptop computer 210 may be configured for use with other portable chemical profiling devices implemented in a manner similar to portable chemical profiling device 200.

In one illustrative example, cause identification system 208 may use a database stored on laptop computer 210 to identify the probable cause of chemical-based event 116. In another illustrative example, cause identification system 208 may be configured to communicate wirelessly with another computer, server, or system located remotely and on which the database is stored to perform the identification.

Together, cause identification system 208 and portable chemical profiling device 200 form chemical investigation system 212. The database may be considered part of or separate from chemical investigation system 212 depending on the implementation. Chemical investigation system 212 may be an example of one manner in which chemical investigation system 400 described in FIG. 4 below may be implemented.

Figure 3:
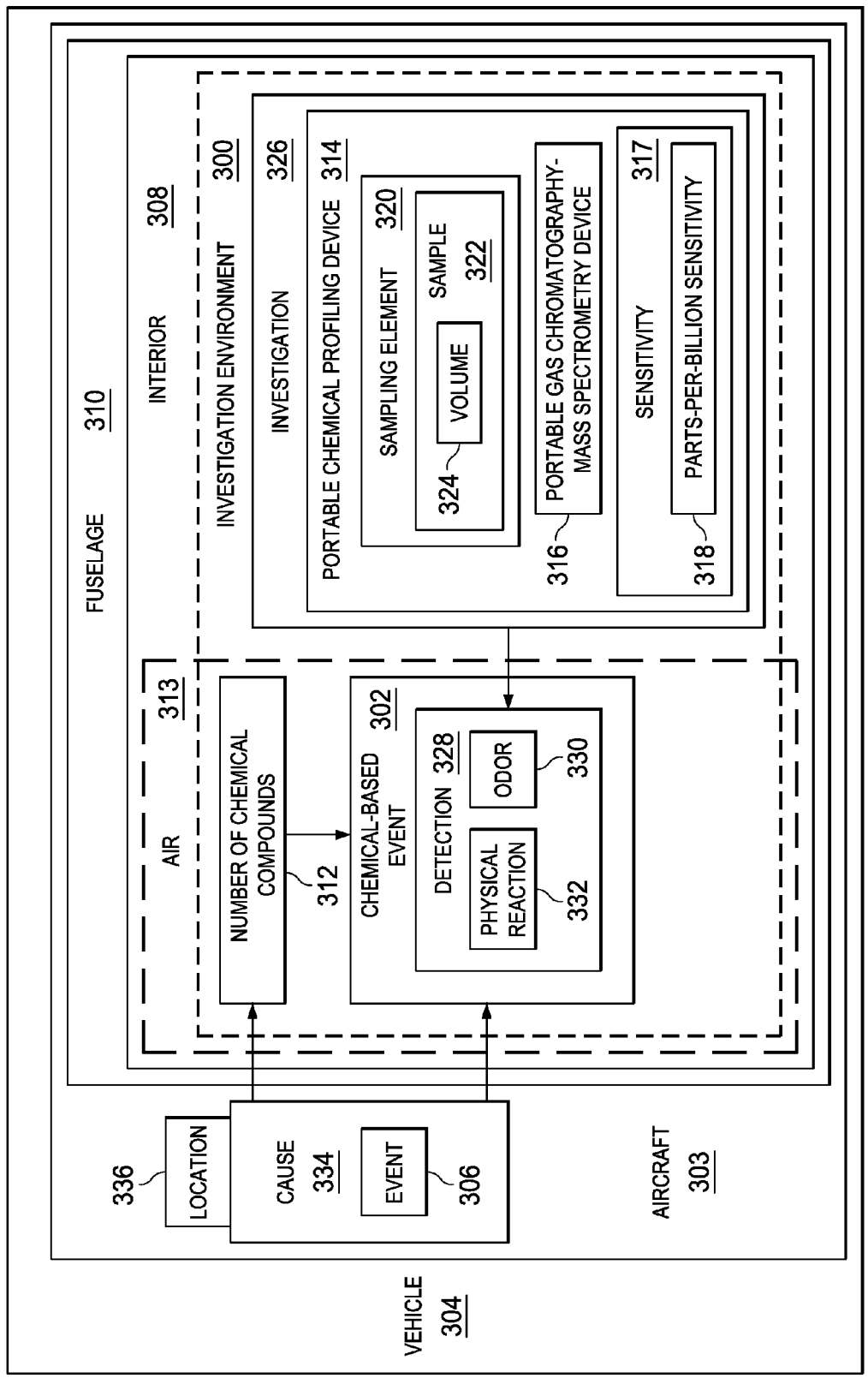
FIG. 3 is an illustration of an investigation environment in the form of a block diagram in accordance with an illustrative embodiment.

With reference now to FIG. 3, an illustration of an investigation environment is depicted in the form of a block diagram in accordance with an illustrative embodiment. In this illustrative example, investigation environment 300 may be an example of an environment in which an investigation of chemical-based event 302 may be performed. Area 118 inside passenger cabin 120 of aircraft 100 in FIGS. 1-2 may be an example of one type of investigation environment 300. Chemical-based event 116 in FIGS. 1-2 may be an example of one type of chemical-based event 302.

Vehicle 304 may take the form of aircraft 303 in this illustrative example. Aircraft 100 in FIGS. 1-2 may be an example of one implementation for aircraft 303. In other illustrative examples, vehicle 304 may take the form of a helicopter, a hovercraft, a spacecraft, a space shuttle, a ship, or some other type of air, water, space, or ground vehicle.

As depicted, event 306 may occur in vehicle 304. Event 306 may take the form of, for example, without limitation, a change in the operation of a system in vehicle 304, a change in the state of vehicle 304, an introduction of a foreign substance inside vehicle 304, or some other type of event. For example, event 306 may be an off-gassing of volatile organic compounds (VOCs), a leakage of battery cell fluid, a problem with a valve, a system being shut-off at the wrong time, a system being turned on at the wrong time, or some other type of event.

Event 306 may lead to chemical-based event 302 occurring within interior 308 of vehicle 304. When vehicle 304 takes the form of aircraft 303, interior 308 may be the inside of fuselage 310 of aircraft 303. For example, event 306 may result in number of chemical compounds 312 being released into air 313 within interior 308 of fuselage 310 of aircraft 303. Number of chemical compounds 312 may, in turn, lead to chemical-based event 302. As used herein, a "number of" items may include one or more items. In this manner, number of chemical compounds 312 may include one or more chemical compounds.

Portable chemical profiling device 314 may be used to investigate chemical-based event 302. Portable chemical profiling device 200 in FIG. 2 may be an example of one implementation for portable chemical profiling device 314.

In one illustrative example, portable chemical profiling device 314 may take the form of portable gas chromatography-mass spectrometry device 316. Portable gas chromatography-mass spectrometry device 316 may combine the techniques of gas liquid chromatography and mass spectrometry to identify the different chemical substances within a sample.

Portable chemical profiling device 314 may be configured to collect samples and generate chemical profiles for those samples. Portable chemical profiling device 314 may have sensitivity 317. Sensitivity 317 may also be referred to as a quantification limit.

In one illustrative example, portable chemical profiling device 314 may have at least parts-per-billion sensitivity 318. In other words, portable chemical profiling device 314 may be capable of identifying the presence of chemical substances in a sample that are present in concentrations of one parts-per-billion (ppb) or less than one parts-per-billion within the sample. In other illustrative examples, portable chemical profiling device 314 may have parts-per-trillion (ppt) sensitivity.

In still other illustrative examples, sensitivity 317 may be quantified in micrograms per liter (µg/L). In other words, portable chemical profiling device 314 may be capable of distinguishing chemical compounds having concentrations in the range of micrograms per liter (µg/L).

Portable chemical profiling device 314 may include sampling element 320. Sampling element 206 in FIG. 2 may be an example of one implementation for sampling element 320. Sampling element 320 may be used to collect samples of air 313.

Sampling element 320 may be capable of collecting samples, such as sample 322, having volume 324. In particular, sampling element 320 may collect sample 322 with volume 324 sufficient to identify number of chemical compounds 312 in sample 322 based on a corresponding chemical profile generated for sample 322 by portable chemical profiling device 314. Volume 324 may be in the range of microliters (µL), milliliters (mL), tens of milliliters, hundreds of milliliters, or liters depending on the implementation.

Portable chemical profiling device 314 may be implemented using any gas chromatograph-mass spectrometer (GC/MS) device capable of being carried by a person, capable of collecting samples with volume 324 sufficient for identifying number of chemical compounds 312 accurately, having at least parts-per-billion sensitivity 318, and capable of measuring multiple chemical compounds simultaneously. As one illustrative example, the HAPSITE® Smart Plus Chemical Identification System, provided by INFICON, may be used to implement portable chemical profiling device 314. The HAPSITE® Smart Plus Chemical Identification System is a portable gas chromatograph-mass spectrometer.

In this manner, portable chemical profiling device 314 may be used to perform investigation 326 of chemical-based event 302 in response to detection 328 of chemical-based event 302. Portable chemical profiling device 314 enables investigation 326 to be performed soon after detection 328 of chemical-based event 302. For example, when vehicle 304 takes the form of aircraft 303, portable chemical profiling device 314 may be stored onboard aircraft 303 such that investigation 326 may be initiated within seconds or minutes of detection 328.

Depending on the type of event 306 that occurs with vehicle 304, chemical-based event 302 may comprise at least one of odor 330 or physical reaction 332. Physical reaction 332 may be the reaction of a human to number of chemical compounds 312 present in air 313. Physical reaction 332 may take the form of, for example, without limitation, watery eyes, a headache, a skin-related symptom, some other type of physical reaction, or some other type of physical reaction.

As used herein, the phrase "at least one of," when used with a list of items, means different combinations of one or more of the listed items may be used and only one of the items in the list may be needed. The item may be a particular object, thing, action, process, or category. In other words, "at least one of" means any combination of items or number of items may be used from the list, but not all of the items in the list may be required.

For example, "at least one of item A, item B, or item C" or "at least one of item A, item B, and item C" may mean item A; item A and item B; item B; item A, item B, and item C; or item B and item C. In some cases, "at least one of item A, item B, and item C" may mean, for example, without limitation, two of item A, one of item B, and ten of item C; four of item B and seven of item C; or some other suitable combination.

Thus, detection 328 of at least one of odor 330 or physical reaction 332 may include the detection of a single odor, a single physical reaction, one odor and one physical reaction, two distinct types of odor and one physical reaction, one odor and three types of physical reactions, or some other combination. In other illustrative examples, chemical-based event 302 may include some other type of detection 328 in addition to at least one of odor 330 or physical reaction 332.

Prior to investigation 326, cause 334 of chemical-based event 302 may be unknown. Additionally, in some cases, location 336 of cause 334 may be unknown. In some illustrative examples, cause 334 may also be referred to as the source of chemical-based event 302.

As depicted in one example, cause 334 may be event 306. However, in other illustrative examples, cause 334 may be an object. An example of one manner in which investigation 326 is conducted to identify cause 334 and location 336 of cause 334 is described in greater detail in FIG. 4 below.

Figure 4:
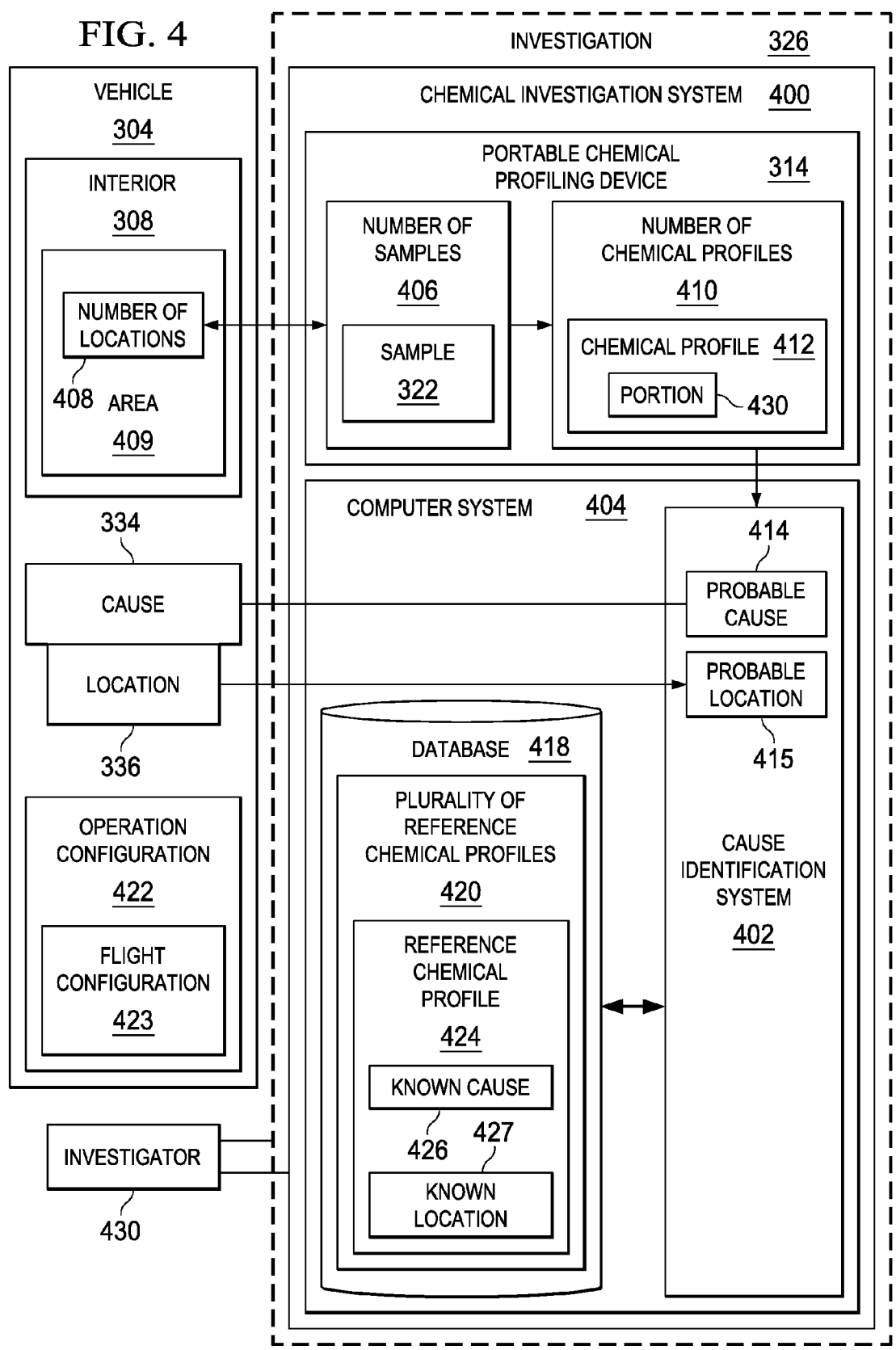
FIG. 4 is an illustration of an investigation in the form of a block diagram in accordance with an illustrative embodiment.

With reference now to FIG. 4, an illustration of investigation 326 from FIG. 3 is depicted in the form of a block diagram in accordance with an illustrative embodiment. Investigation 326 may be performed using chemical investigation system 400. Chemical investigation system 400 includes both portable chemical profiling device 314 from FIG. 3 and cause identification system 402. Cause identification system 402 may be an example of one implementation for cause identification system 208 described in FIG. 2. When cause 334 is referred to as a source, cause identification system 402 may be referred to as a source identification system.

Cause identification system 402 may be implemented using hardware, software, or both. When software is used, the operations performed by cause identification system 402 may be implemented using, for example, without limitation, program code configured to run on a processor unit. When firmware is used, the operations performed by cause identification system 402 may be implemented using, for example, without limitation, program code and data and stored in persistent memory to run on a processor unit.

When hardware is employed, the hardware may include one or more circuits that operate to perform the operations performed by cause identification system 402. Depending on the implementation, the hardware may take the form of a circuit system, an integrated circuit, an application specific integrated circuit (ASIC), a programmable logic device, or some other suitable type of hardware device configured to perform any number of operations.

A programmable logic device may be configured to perform certain operations. The device may be permanently configured to perform these operations or may be reconfigurable. A programmable logic device may take the form of, for example, without limitation, a programmable logic array, a programmable array logic, a field programmable logic array, a field programmable gate array, or some other type of programmable hardware device.

In some illustrative examples, the operations and processes performed by cause identification system 402 may be performed using organic components integrated with inorganic components. In some cases, the operations and processes may be performed by entirely organic components, excluding a human being. As one illustrative example, circuits in organic semiconductors may be used to perform these operations and processes.

In one illustrative example, cause identification system 402 may be implemented in computer system 404. Laptop computer 210 in FIG. 2 may be an example of one implementation for computer system 404. Although cause identification system 208 is depicted being implemented on laptop computer 210, cause identification system 208 may be implemented on a different type of computer system or processor unit. For example, cause identification system 208 may be implemented on a tablet computer or a hybrid laptop-tablet computer in some illustrative examples.

Depending on the implementation, computer system 404 may be stored inside vehicle 304 for easy and quick access to cause identification system 402 such that investigation 326 may be performed soon after detection 328 of chemical-based event 302 in FIG. 3. Of course, in some illustrative examples, computer system 404 may be stored off-board until chemical-based event 302 has been detected.

In response to detection 328 of chemical-based event 302 as described in FIG. 3, investigator 430 may perform investigation 326 using chemical investigation system 400. Investigator 430 may be, for example, but is not limited to, a passenger of vehicle 304, an operator of vehicle 304, an engineer, a technician, a chemical expert, a systems expert, or some other type of investigator interested in determining cause 334 and location 336 of cause 334 of chemical-based event 302.

In particular, investigator 430 may begin by using portable chemical profiling device 314 of chemical investigation system 400 to collect number of samples 406 from number of locations 408 within interior 308 of vehicle 304 from FIG. 3. Number of locations 408 for sampling may be selected from within area 409 inside vehicle 304 in which chemical-based event 302 in FIG. 3 is most strongly detected. For example, without limitation, area 409 may be the space within which odor 330 in FIG. 3 is most strongly detected or where physical reaction 332 is most strongly experienced.

Portable chemical profiling device 314 may generate number of chemical profiles 410 for number of samples 406 on-site. In particular, portable chemical profiling device 314 generates a corresponding chemical profile for each of number of samples 406 to form number of chemical profiles 410.

Sample 322 from FIG. 3 may be an example of one of number of samples 406. Chemical profile 412 in number of chemical profiles 410 may be a corresponding chemical profile for sample 322. Chemical profile 412 may include a breakdown of the various chemical compounds within sample 322 and the concentration of each of those chemical compounds in sample 322.

Portable chemical profiling device 314 is used to generate number of chemical profiles 410 for number of samples 406 on-site. In other words, number of chemical profiles 410 may be generated inside vehicle 304. When vehicle 304 takes the form of aircraft 303, as described in FIG. 3, number of chemical profiles 410 may be generated while still onboard aircraft 303 after collecting number of samples 406 without significant delay. For example, number of chemical profiles 410 may be generated within seconds or minutes of obtaining number of samples 406, depending on the number of samples 406 collected.

Number of chemical profiles 410 may be sent to cause identification system 402 for processing. In one illustrative example, portable chemical profiling device 314 may be configured to send number of chemical profiles 410 directly to cause identification system 402 on computer system 404 using any number of wired communications links, wireless communications links, optical communications links, or combination thereof. Depending on the implementation, computer system 404 is located onboard vehicle 304. In other cases, computer system 404 may be located off-board, or off of vehicle 304.

Cause identification system 402 uses at least one of number of chemical profiles 410 and database 418 to identify probable cause 414 of chemical-based event 302 in FIG. 3. When cause 334 is referred to as a source, probable cause 414 may be referred to as a probable source.

In some cases, depending on the type of probable cause 414 identified and the information stored in database 418, cause identification system 402 may also identify probable location 415 for probable cause 414. In one illustrative example, probable location 415 may be a general location, such as a general area inside vehicle 304. In another example, probable location 415 may be a more precise location, such as a location at, on, or around some object or component in vehicle 304. In yet another illustrative example, probable location 415 may be a two-dimensional or three-dimensional location with respect to a reference coordinate system for vehicle 304. For example, the probable location 415 may be a two-dimensional or three-dimensional location with respect to an aircraft coordinate system for aircraft 303 in FIG. 3. In some cases, once probable cause 414 and probable location 415 have been identified, investigator 430 may then perform further investigation to confirm whether probable cause 414 is indeed cause 334 of chemical-based event 302 and whether probable location 415 is indeed location 336 of cause 334.

In this illustrative example, database 418 may be located on computer system 404. However, in other illustrative examples, database 418 may be located on some other computer, server, or other storage device located remotely with respect to computer system 404. Cause identification system 402 on computer system 404 may be configured to access and interact with database 418 using any number of wired communications links, wireless communications links, optical communications links, or combination thereof.

For example, cause identification system 402 may select a particular chemical profile, such as chemical profile 412, from number of chemical profiles 410 for processing. Cause identification system 402 compares chemical profile 412 to plurality of reference chemical profiles 420 stored on database 418 to determine whether the particular chemical profile 412 matches any of plurality of reference chemical profiles 420. Plurality of reference chemical profiles 420 may be associated with a plurality of known causes of chemical-based events. In particular, each of plurality of reference chemical profiles 420 may be associated with at least one of a known chemical-based event or a known cause.

Reference chemical profile 424 may be an example of one of plurality of reference chemical profiles 420. Reference chemical profile 424 may be a chemical profile for one or more chemical compounds known to cause at least one of an odor or physical reaction. Further, reference chemical profile 424 may be associated with known cause 426 of the one or more chemical compounds that caused the at least one of the odor or physical reaction.

If chemical profile 412 substantially matches, for example, reference chemical profile 424 within selected tolerances, known cause 426 associated with reference chemical profile 424 may then be identified as probable cause 414 of chemical-based event 302. In some cases, database 418 may also include known location 427 for known cause 426 that is then identified as probable location 415 of probable cause 414.

In other illustrative examples, probable location 415 may be identified prior to the identification of probable cause 414. For example, probable location 415 of probable cause 414 may be identified based on the location inside vehicle 304 where sample 322 corresponding to chemical profile 412 was collected. In some illustrative examples, probable location 415 may be identified as at or around the location at which chemical-based event 302 was most strongly detected. In one illustrative example, investigator 430 may record the location of where chemical-based event 302 was detected, or most strongly detected depending on the implementation, as probable location 415.

Depending on the implementation, identification of probable location 415 may help narrow down the potential causes for chemical-based event 302 from which probable cause 414 is selected. As one illustrative example, investigator 430 may record the location at which chemical-based event 302 was most strongly detected as probable location 415 and enter probable location 415 as input into cause identification system 402. Cause identification system 402 may use probable location 415 to filter or narrow the reference chemical profiles in plurality of reference chemical profiles 420 in database 418 to which chemical profile 412 is compared.

Cause identification system 402 may obtain operation configuration 422 of vehicle 304 at a time at which chemical-based event 302 was detected. Operation configuration 422 may then be linked to cause 334 of chemical-based event 302. Operation configuration 422 may include the configuration or state of each of various systems and components in vehicle 304.

As one illustrative example, when vehicle 304 takes the form of aircraft 303, operation configuration 422 may be flight configuration 423 for aircraft 303. Flight configuration 423 may include, for example, without limitation, the state of the flight control system, the configuration of the different control surfaces of aircraft 303, the state of the engine systems of aircraft 303, and the state or configuration of other types of systems of aircraft 303 at the time chemical-based event 302 was detected. Flight configuration 423 may be obtained from, for example, without limitation, a flight control system onboard aircraft 303.

In some cases, none of number of chemical profiles 410 may substantially match a reference chemical profile in plurality of reference chemical profiles 420 within selected tolerances. In these cases, further testing may need to be performed to identify cause 334. An example of one manner in which further testing may be performed to identify cause 334 is described in greater detail in the flowchart depicted in FIG. 7 further below.

Once cause 334 of chemical-based event 302 is identified, at least a portion of at least one of number of chemical profiles 410 may be added to database 418 as a new reference chemical profile in plurality of reference chemical profiles 420 and cause 334 added to database 418 as being a new known cause associated with the new chemical profile in database 418. In this manner, database 418 may be dynamic and built over time to contain reference chemical profiles for a variety of different causes of chemical-based events.

The illustrations of investigation environment 300 in FIG. 3 and investigation 326 and chemical investigation system 400 in FIG. 4 are not meant to imply physical or architectural limitations to the manner in which an illustrative embodiment may be implemented. Other components in addition to or in place of the ones illustrated may be used. Some components may be optional. Also, the blocks are presented to illustrate some functional components. One or more of these blocks may be combined, divided, or combined and divided into different blocks when implemented in an illustrative embodiment. For example, although investigation environment 300 is described as being located inside a vehicle, investigation environment 300 may be located inside a satellite station, an offshore oil platform, or some other type of environment or area.

Figure 5:
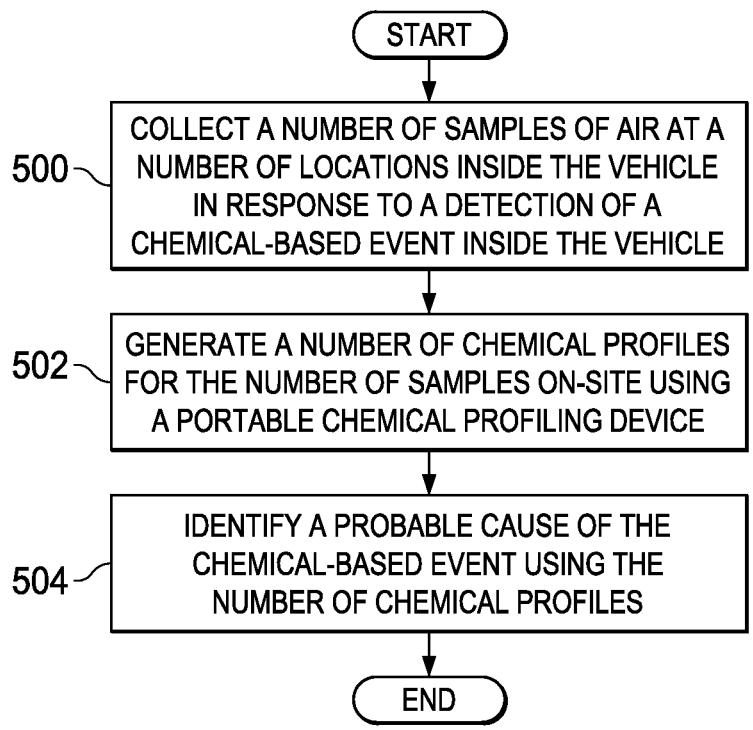
FIG. 5 is an illustration of a process for investigating a chemical-based event inside a vehicle in the form of a flowchart in accordance with an illustrative embodiment.

With reference now to FIG. 5, an illustration of a process for investigating a chemical-based event inside a vehicle is depicted in the form of a flowchart in accordance with an illustrative embodiment. The process illustrated in FIG. 5 may be implemented using chemical investigation system 400 in FIG. 4.

The process may begin by collecting a number of samples of air at a number of locations inside the vehicle in response to a detection of the chemical-based event inside the vehicle (operation 500). The collection of the number of samples collected in operation 500 may be performed using, for example, portable chemical profiling device 314 in FIGS. 3-4. In one illustrative example, the vehicle may be an aircraft, such as aircraft 100 in FIG. 1. In another illustrative example, the vehicle may take the form of a spacecraft, a space shuttle, a ship, or some other type of vehicle.

In some cases, the number of samples may be collected while the vehicle is in operation. As one illustrative example, when the vehicle is an aircraft, the number of samples may be collected while the aircraft is in flight. In another example, when the vehicle is a space shuttle, the number of samples may be generated while the space shuttle is in flight in space beyond the atmosphere of the Earth.

Thereafter, a number of chemical profiles may be generated for the number of samples on-site using a portable chemical profiling device (operation 502). Generating the number of chemical profiles on-site in operation 502 means generating the number of chemical profiles while onboard the vehicle. The number of chemical profiles may be generated without significant delay. For example, the number of chemical profiles may be generated within seconds, minutes, or tens of minutes.

A probable cause of the chemical-based event may then be identified using the number of chemical profiles (operation 504), with the process terminating thereafter. In some cases, a probable location of the probable cause of the chemical-based event may also be identified in operation 504.

Figure 6:
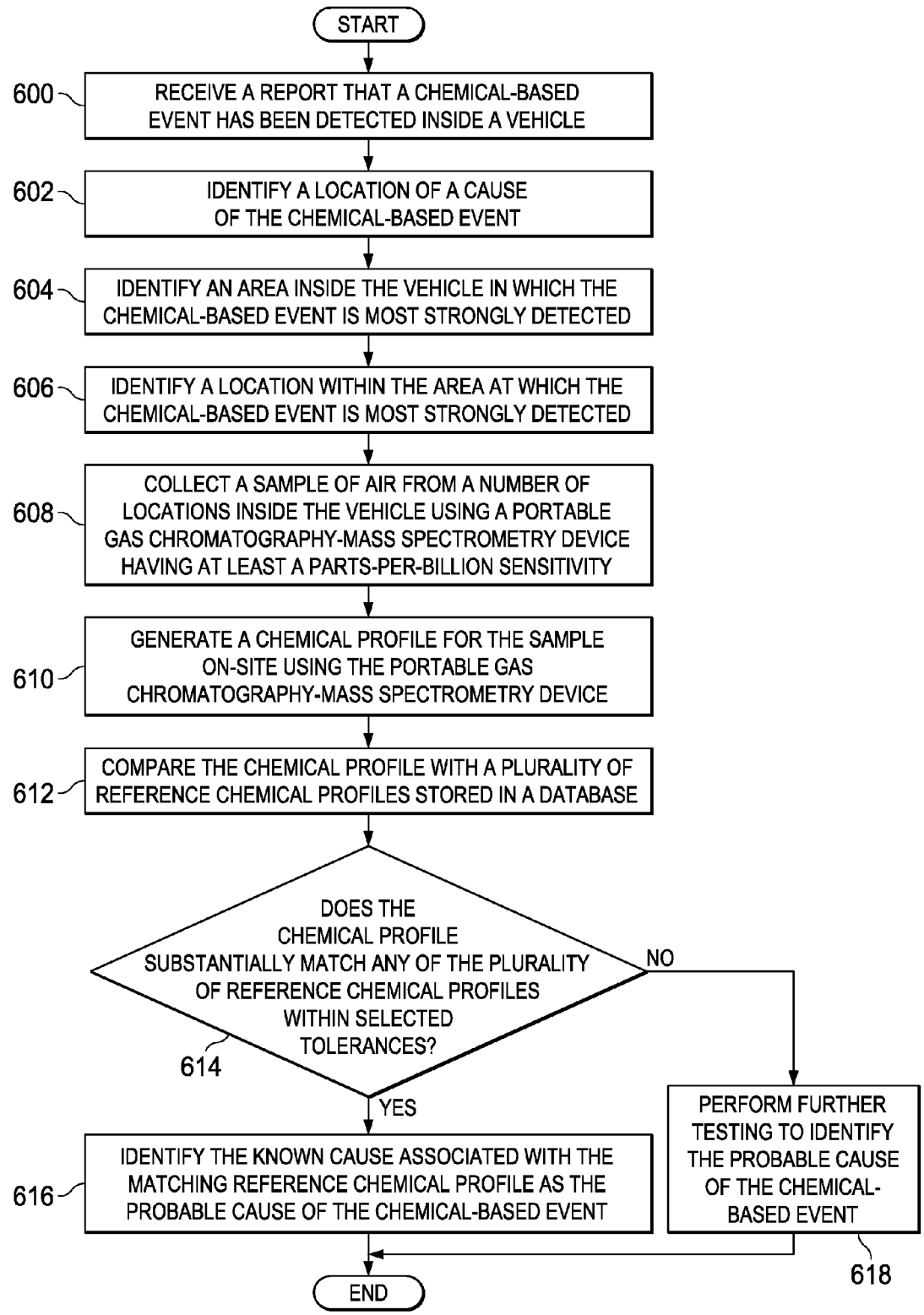
FIG. 6 is an illustration of a process for investigating a chemical-based event inside a vehicle in the form of a flowchart in accordance with an illustrative embodiment.

With reference now to FIG. 6, an illustration of a process for investigating a chemical-based event inside a vehicle is depicted in the form of a flowchart in accordance with an illustrative embodiment. The process illustrated in FIG. 5 may be implemented using chemical investigation system 400 in FIG. 4 and, in particular, portable chemical profiling device 314 in FIGS. 3 and 4.

The process begins by receiving a report that a chemical-based event has been detected inside a vehicle (operation 600). In operation 600, the chemical-based event may comprise at least one of an odor inside the vehicle or a physical reaction of a human to a number of chemical compounds present in the air inside the vehicle.

Next, a location of a cause of the chemical-based event is identified (operation 602). In one illustrative example, this location may be a probable location of the probable cause of the chemical-based event. In operation 602, the location may be a general location inside the vehicle. An example of one manner in which the location of the cause of the chemical-based event may be identified when the vehicle is an aircraft is described in greater detail in FIG. 8 below.

Thereafter, an area inside the vehicle in which the chemical-based event is most strongly detected is identified (operation 604). In operation 604, the area identified may be the area in which the chemical-based event was strongest when the chemical-based event was first detected or the area in which the chemical-based event is most strongly detected by an investigator at the time of investigation.

Next, a location within the area at which the chemical-based event is most strongly detected is identified (operation 606). A sample of air is collected from the number of locations inside the vehicle using a portable gas chromatography-mass spectrometry device having at least a parts-per-billion sensitivity (operation 608).

Thereafter, a chemical profile is generated for the sample on-site using the portable gas chromatography-mass spectrometry device (operation 610). In other words, a chemical profile may be generated by the portable gas chromatography-mass spectrometry device for the sample onboard the vehicle without significant delay after sample collection. The chemical profile may be comprised of chromatogram/mass spectral data for the corresponding sample. The sample may have a volume sufficient to identify a number of chemical compounds in the sample based on the corresponding chemical profile.

Thereafter, the chemical profile may be compared with a plurality of reference chemical profiles stored in a database (operation 612). A determination is made as to whether the chemical profile substantially matches any of the plurality of reference chemical profiles within selected tolerances (operation 614). In making this determination in operation 614, a portion of the chemical profile is identified as corresponding to the chemical-based event in one illustrative example. This portion of the chemical profile is compared to the plurality of reference chemical profiles in operation 614.

If the chemical profile substantially matches any of the plurality of reference chemical profiles, the known cause associated with the matching reference chemical profile is identified as the probable cause of the chemical-based event (operation 616), with the process terminating thereafter. In some cases, the probable cause identified in operation 616 may be considered to be the cause of the chemical-based event. In other cases, further investigation may need to be performed to confirm whether or not the probable cause is indeed the cause of the chemical-based event. In this manner, the cause and the general location of the cause of the chemical-based event may be identified. Any number of actions may then be taken to address the cause of the chemical-based event.

With reference again to operation 614, if the chemical profile does not substantially match any of the plurality of reference chemical profiles, further testing is performed to identify the probable cause of the chemical-based event (operation 618), with the process terminating thereafter. An example of one manner in which operation 618 may be performed is described in greater detail in FIG. 7 below.

Figure 7:
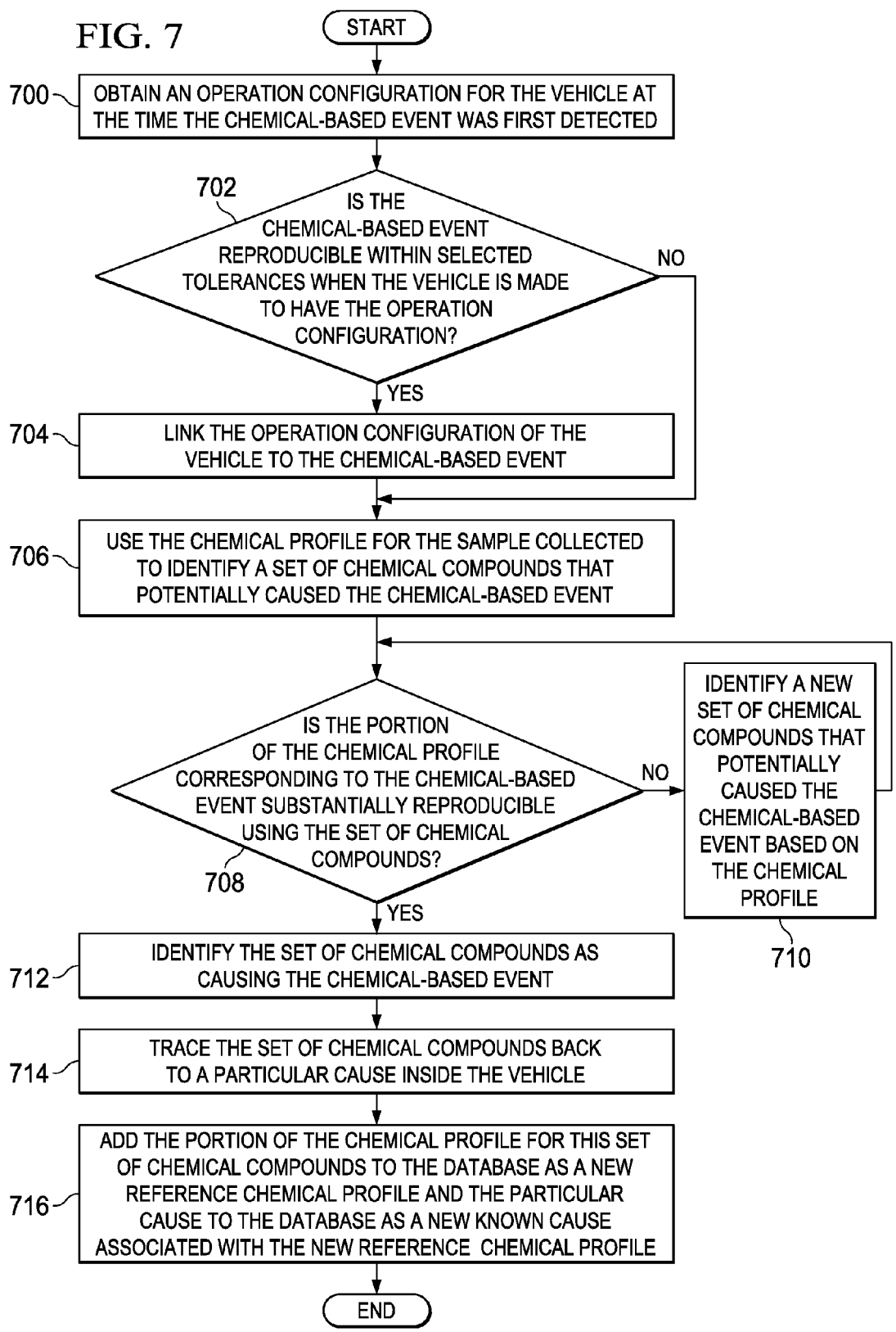
FIG. 7 is an illustration of a process for performing further testing to identify the cause of a chemical-based event in the form of a flowchart in accordance with an illustrative embodiment.

With reference now to FIG. 7, an illustration of a process for performing further testing to identify the cause of a chemical-based event is depicted in the form of a flowchart in accordance with an illustrative embodiment. The process illustrated in FIG. 7 may be an example of one manner in which operation 618 may be performed.

The process begins by obtaining an operation configuration for the vehicle at the time the chemical-based event was first detected (operation 700). In some cases, this time may be noted on the report received in operation 600 in FIG. 6. When the vehicle is an aircraft, the operation configuration may be referred to as the flight configuration of the aircraft.

Next, a determination is made as to whether the chemical-based event is reproducible within selected tolerances when the vehicle is made to have the operation configuration (operation 702). If the chemical-based event is reproducible, the operation configuration of the vehicle is linked to the chemical-based event (operation 704). The process then proceeds to operation 706 described below. With reference again to operation 702, if the chemical-based event is not reproducible, the process proceeds directly to operation 706 described below.

The chemical profile for the sample collected is then used to identify a set of chemical compounds that potentially caused the chemical-based event (operation 706). In one illustrative example, in operation 706, the set of chemical compounds corresponding to a portion of the chemical profile corresponding to the chemical-based event is identified. The set of chemical compounds may include one or more chemical compounds.

A determination is then made as to whether the portion of the chemical profile corresponding to the chemical-based event is substantially reproducible using the set of chemical compounds (operation 708). If the portion of the chemical profile is not reproducible, a new set of chemical compounds that potentially caused the chemical-based event is identified based on chemical profile (operation 710), with the process then returning to operation 708 as described above.

With reference again to operation 708, if the portion of the chemical profile is reproducible, the set of chemical compounds is identified as causing the chemical-based event (operation 712). The set of chemical compounds may then be traced back to a particular cause inside the vehicle (operation 714). The portion of the chemical profile for this set of chemical compounds is then added to the database as a new reference chemical profile and the particular cause is added to the database as a new known cause associated with the new reference chemical profile (operation 716), with the process terminating thereafter. In this manner, the database may be a dynamic database in the new reference chemical profiles and associated known causes may be added to the database.

Figure 8:
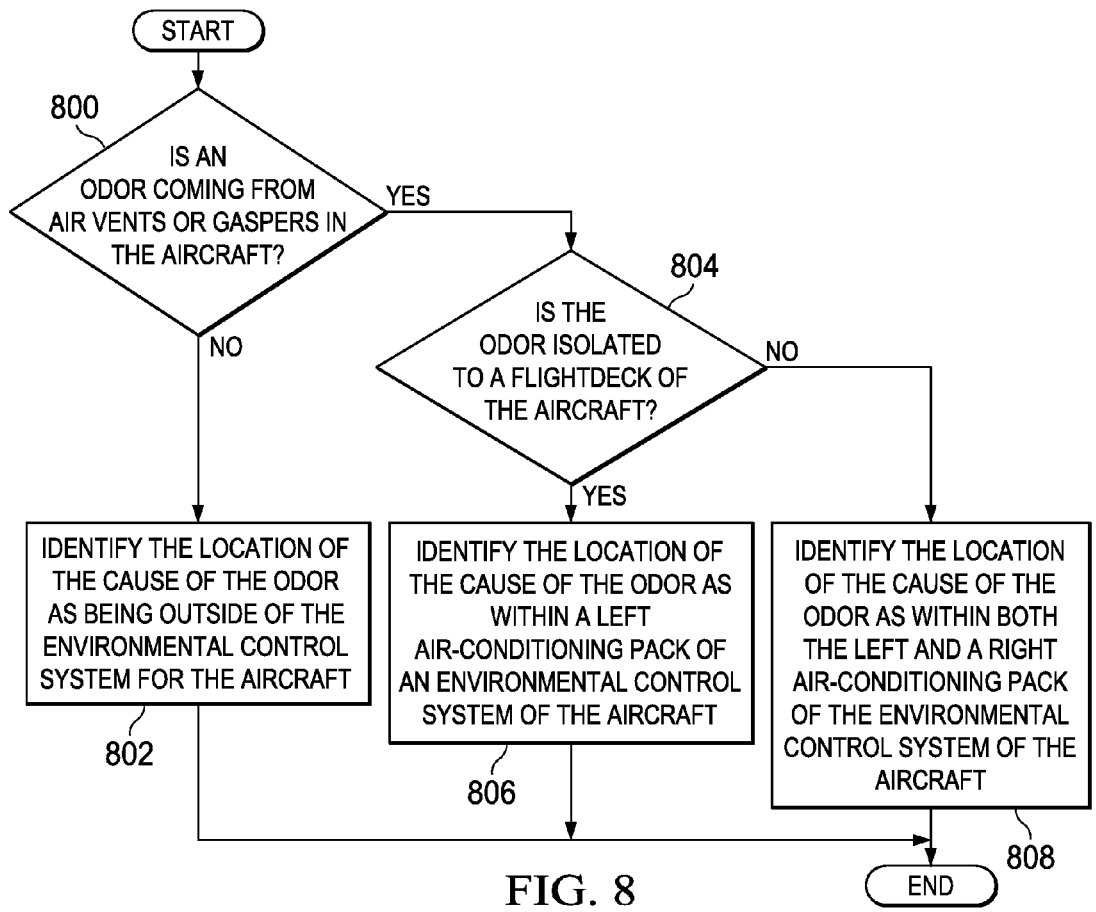
FIG. 8 is an illustration of a process for identifying the location of the cause of a chemical-based event that is detected inside an aircraft in the form of a flowchart in accordance with an illustrative embodiment.

With reference now to FIG. 8, an illustration of a process for identifying the location of the cause of a chemical-based event that is detected inside an aircraft is depicted in the form of a flowchart in accordance with an illustrative embodiment. The process illustrated in FIG. 8 may be an example of one manner in which operation 602 in FIG. 6 may be performed when the vehicle is an aircraft. Further, this process may be used when the chemical-based event is an odor.

The process begins by determining whether an odor is coming from air vents or gaspers in the aircraft (operation 800). Gaspers are the air outlets above passenger seats in passenger aircraft.

If the odor is not coming from the air vents or the gaspers, the location of the cause of the odor is identified as being outside of the environmental control system for the aircraft (operation 802), with the process terminating thereafter. Otherwise, if the odor is coming from the air vents or the gaspers, a determination is made as to whether the odor is isolated to a flightdeck of the aircraft (operation 804).

If the odor is isolated to the flightdeck, the location of the cause of the odor is identified as within a left air-conditioning pack of an environmental control system of the aircraft (operation 806), with the process terminating thereafter. Otherwise, if the odor is not isolated to the flightdeck, the location of the cause of the odor is identified as within both the left and a right air-conditioning pack of the environmental control system of the aircraft (operation 808), with the process terminating thereafter. In this manner, a general location of the cause of the odor may be identified.

The flowcharts and block diagrams in the different depicted embodiments illustrate the architecture, functionality, and operation of some possible implementations of apparatuses and methods in an illustrative embodiment. In this regard, each block in the flowcharts or block diagrams may represent a module, a segment, a function, a portion of an operation or step, some combination thereof.

In some alternative implementations of an illustrative embodiment, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram.

Figure 9:
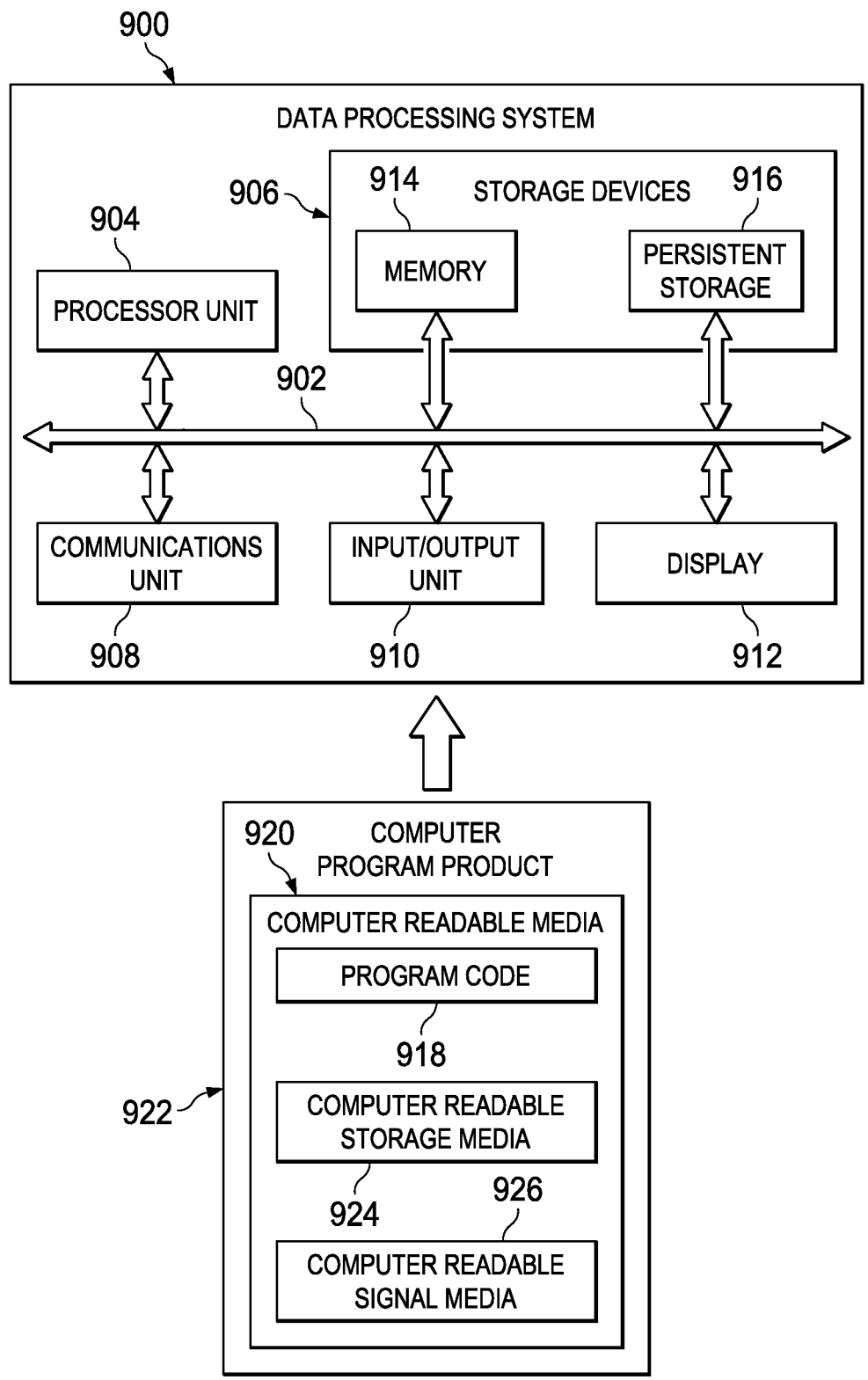
FIG. 9 is an illustration of a data processing system in the form of a block diagram in accordance with an illustrative embodiment.

Turning now to FIG. 9, an illustration of a data processing system is depicted in the form of a block diagram in accordance with an illustrative embodiment. Data processing system 900 may be used to implement computer system 404 in FIG. 4. As depicted, data processing system 900 includes communications framework 902, which provides communications between processor unit 904, storage devices 906, communications unit 908, input/output unit 910, and display 912. In some cases, communications framework 902 may be implemented as a bus system.

Processor unit 904 is configured to execute instructions for software to perform a number of operations. Processor unit 904 may comprise at least one of a number of processors, a multi-processor core, or some other type of processor, depending on the implementation. In some cases, processor unit 904 may take the form of a hardware unit, such as a circuit system, an application specific integrated circuit (ASIC), a programmable logic device, or some other suitable type of hardware unit.

Instructions for the operating system, applications and programs run by processor unit 904 may be located in storage devices 906. Storage devices 906 may be in communication with processor unit 904 through communications framework 902. As used herein, a storage device, also referred to as a computer readable storage device, is any piece of hardware capable of storing information on a temporary basis, a permanent basis, or both. This information may include, but is not limited to, data, program code, other information, or some combination thereof.

Memory 914 and persistent storage 916 are examples of storage devices 906. Memory 914 may take the form of, for example, a random access memory or some type of volatile or non-volatile storage device. Persistent storage 916 may comprise any number of components or devices. For example, persistent storage 916 may comprise a hard drive, a flash memory, a rewritable optical disk, a rewritable magnetic tape, or some combination of the above. The media used by persistent storage 916 may or may not be removable.

Communications unit 908 allows data processing system 900 to communicate with other data processing systems, devices, or both. Communications unit 908 may provide communications using physical communications links, wireless communications links, or both.

Input/output unit 910 allows input to be received from and output to be sent to other devices connected to data processing system 900. For example, input/output unit 910 may allow user input to be received through a keyboard, a mouse, some other type of input device, or a combination thereof. As another example, input/output unit 910 may allow output to be sent to a printer connected to data processing system 900.

Display 912 is configured to display information to a user. Display 912 may comprise, for example, without limitation, a monitor, a touch screen, a laser display, a holographic display, a virtual display device, some other type of display device, or a combination thereof.

In this illustrative example, the processes of the different illustrative embodiments may be performed by processor unit 904 using computer-implemented instructions. These instructions may be referred to as program code, computer usable program code, or computer readable program code and may be read and executed by one or more processors in processor unit 904.

In these examples, program code 918 is located in a functional form on computer readable media 920, which is selectively removable, and may be loaded onto or transferred to data processing system 900 for execution by processor unit 904. Program code 918 and computer readable media 920 together form computer program product 922. In this illustrative example, computer readable media 920 may be computer readable storage media 924 or computer readable signal media 926.

Computer readable storage media 924 is a physical or tangible storage device used to store program code 918 rather than a medium that propagates or transmits program code 918. Computer readable storage media 924 may be, for example, without limitation, an optical or magnetic disk or a persistent storage device that is connected to data processing system 900.

Alternatively, program code 918 may be transferred to data processing system 900 using computer readable signal media 926. Computer readable signal media 926 may be, for example, a propagated data signal containing program code 918. This data signal may be an electromagnetic signal, an optical signal, or some other type of signal that can be transmitted over physical communications links, wireless communications links, or both.

The illustration of data processing system 900 in FIG. 9 is not meant to provide architectural limitations to the manner in which the illustrative embodiments may be implemented. The different illustrative embodiments may be implemented in a data processing system that includes components in addition to or in place of those illustrated for data processing system 900. Further, components shown in FIG. 9 may be varied from the illustrative examples shown.

Figure 10:
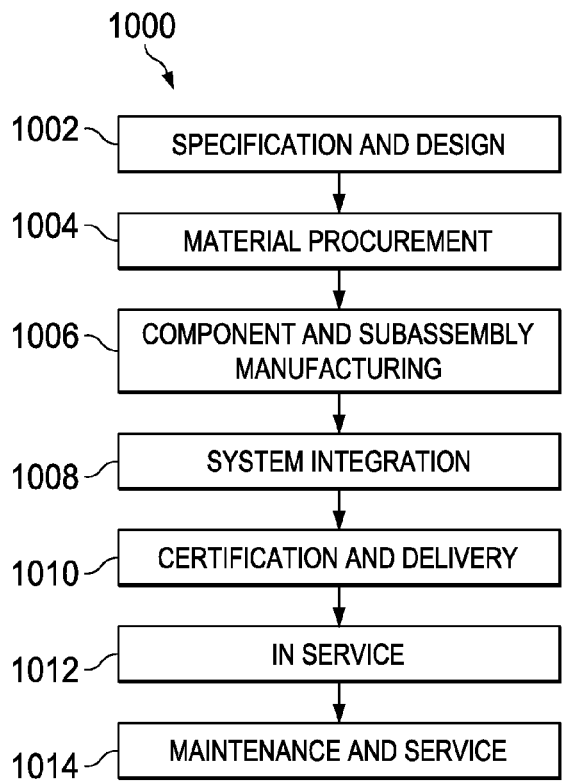
FIG. 10 is an illustration of an aircraft manufacturing and service method in the form of a block diagram in accordance with an illustrative embodiment.
Figure 11:
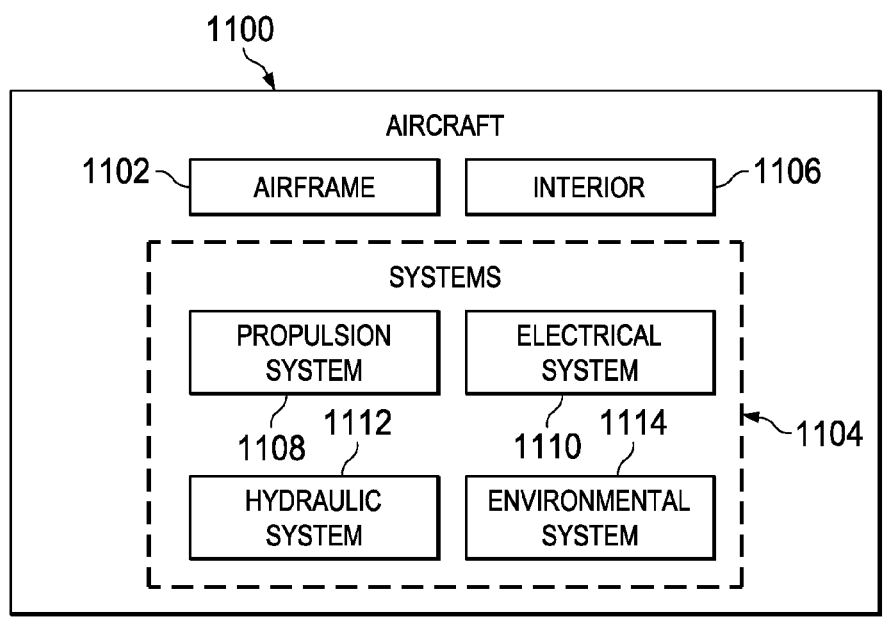
FIG. 11 is an illustration of an aircraft in the form of a block diagram in which an illustrative embodiment may be implemented.

The illustrative embodiments of the disclosure may be described in the context of aircraft manufacturing and service method 1000 as shown in FIG. 10 and aircraft 1100 as shown in FIG. 11. Turning first to FIG. 10, an illustration of an aircraft manufacturing and service method is depicted in the form of a block diagram in accordance with an illustrative embodiment. During pre-production, aircraft manufacturing and service method 1000 may include specification and design 1002 of aircraft 1100 in FIG. 11 and material procurement 1004.

During production, component and subassembly manufacturing 1006 and system integration 1008 of aircraft 1100 in FIG. 11 takes place. Thereafter, aircraft 1100 in FIG. 11 may go through certification and delivery 1010 in order to be placed in service 1012. While in service 1012 by a customer, aircraft 1100 in FIG. 11 is scheduled for routine maintenance and service 1014, which may include modification, reconfiguration, refurbishment, and other maintenance or service.

Each of the processes of aircraft manufacturing and service method 1000 may be performed or carried out by at least one of a system integrator, a third party, or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 11, an illustration of an aircraft is depicted in the form of a block diagram in which an illustrative embodiment may be implemented. In this example, aircraft 1100 is produced by aircraft manufacturing and service method 1000 in FIG. 10 and may include airframe 1102 with plurality of systems 1104 and interior 1106. Examples of systems 1104 include one or more of propulsion system 1108, electrical system 1110, hydraulic system 1112, and environmental system 1114. Any number of other systems may be included. Although an aerospace example is shown, different illustrative embodiments may be applied to other industries, such as the automotive industry.

Apparatuses and methods embodied herein may be employed during at least one of the stages of aircraft manufacturing and service method 1000 in FIG. 10. In particular, chemical investigation system 400 from FIG. 4, and in particular, portable chemical profiling device 314 described in FIGS. 3-4, may be used during any one of the stages of aircraft manufacturing and service method 1000. For example, without limitation, chemical investigation system 400 from FIG. 4 may be used to perform investigations of undesired odors that occur during operation of or testing of aircraft 1100 during at least one of component and subassembly manufacturing 1006, system integration 1008, certification and delivery 1010, in service 1012, routine maintenance and service 1014, or some other stage of aircraft manufacturing and service method 1000.

In one illustrative example, components or subassemblies produced in component and subassembly manufacturing 1006 in FIG. 10 may be fabricated or manufactured in a manner similar to components or subassemblies produced while aircraft 1100 is in service 1012 in FIG. 10. As yet another example, one or more apparatus embodiments, method embodiments, or a combination thereof may be utilized during production stages, such as component and subassembly manufacturing 1006 and system integration 1008 in FIG. 10. One or more apparatus embodiments, method embodiments, or a combination thereof may be utilized while aircraft 1100 is in service 1012, during maintenance and service 1014 in FIG. 10, or both. The use of a number of the different illustrative embodiments may substantially expedite the assembly of and reduce the cost of aircraft 1100.

The description of the different illustrative embodiments has been presented for purposes of illustration and description, and is not intended to be exhaustive or limited to the embodiments in the form disclosed. Many modifications and variations will be apparent to those of ordinary skill in the art. Further, different illustrative embodiments may provide different features as compared to other desirable embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A method for investigating a chemical-based event inside a vehicle without significant delay, the method comprising:
   collecting a number of samples of air at a number of locations inside the vehicle in response to a detection of the chemical-based event inside the vehicle;
   generating a number of chemical profiles for the number of samples on-site using a portable chemical profiling device;
   identifying a probable location of the chemical-based event relative to a vehicle reference coordinate system based on relative concentrations of the chemical profiles for the number of samples;
   identifying an operation configuration of the vehicle at a time at which the chemical-based event was detected; and
   identifying a probable cause of the chemical-based event using the number of chemical profiles, the probable location, and the operation configuration of the vehicle.

2. The method of claim 1 further comprising:
   detecting the chemical-based event, wherein the chemical-based event comprises at least one of an odor inside the vehicle or a physical reaction of a human to a number of chemical compounds present in the air.

3. The method of claim 1 further comprising:
   selecting the number of locations from within the vehicle reference coordinate system and corresponding to an area inside the vehicle in which the chemical-based event is most strongly detected.

4. The method of claim 1, wherein collecting the number of samples comprises:
   collecting each of the number of samples of the air such that the each of the number of samples has a volume sufficient to identify a number of chemical compounds in the each of the number of samples based on a corresponding chemical profile in the number of chemical profiles generated.

5. The method of claim 1, wherein identifying the probable cause of the chemical-based event comprises:
   selecting at least one particular chemical profile from the number of chemical profiles generated; and
   comparing the particular chemical profile to a plurality of reference chemical profiles to determine whether the particular chemical profile substantially matches any of the plurality of reference chemical profiles, wherein each of the plurality of reference chemical profiles is associated with a known cause in the vehicle.

6. The method of claim 5 further comprising:
   determining whether the chemical-based event is reproducible within selected tolerances when the vehicle is made to have the operation configuration; and
   linking the operation configuration of the vehicle to the chemical-based event in response to a determination that the chemical-based event is reproducible within the selected tolerances when the vehicle is made to have the operation configuration.

7. The method of claim 6 further comprising:
   identifying a set of chemical compounds that potentially caused the chemical-based event based on the particular chemical profile;
   determining whether a portion of the particular chemical profile corresponding to the chemical-based event is substantially reproducible using the set of chemical compounds;
   identifying the set of chemical compounds as causing the chemical-based event in response to a determination that the portion of the particular chemical profile corresponding to the chemical-based event is substantially reproducible using the set of chemical compounds; and identifying a new set of chemical compounds that potentially caused the chemical-based event based on the particular chemical profile in response to a determination that the portion of the particular chemical profile corresponding to the chemical-based event is not substantially reproducible using the set of chemical compounds.

8. The method of claim 1, wherein the vehicle is an aircraft and further comprising:
identifying a probable location of the chemical-based event with respect to the aircraft; and
performing further investigation to confirm whether the probable cause identified is a cause of the chemical-based event and whether the probable location identified is a location of the chemical-based event.

9. A method for investigating a chemical-based event inside an aircraft without significant delay, the method comprising:
collecting a number of samples of air at a number of locations inside the aircraft in response to a detection of the chemical-based event inside the aircraft;
generating a number of chemical profiles for the number of samples on-site using a portable chemical profiling device;
identifying a probable location of the chemical-based event relative to a vehicle reference coordinate system based on relative concentrations of the chemical profiles for the number of samples;
identifying an operation configuration of the aircraft at a time at which the chemical-based event was detected; and
identifying a probable cause of the chemical-based event using the number of chemical profiles, the probable location, and the operation configuration of the vehicle.

10. The method of claim 9, wherein generating the number of chemical profiles comprises:
generating the number of chemical profiles for the number of samples using a portable gas chromatography-mass spectrometry device having at least a parts-per-billion sensitivity.

11. The method of claim 9, wherein collecting the number of samples of the air comprises:
collecting each of the number of samples of the air such that the each of the number of samples has a volume sufficient to identify a number of chemical compounds in the each of the number of samples based on a corresponding chemical profile in the number of chemical profiles generated.

12. The method of claim 9, wherein identifying the probable cause of the chemical-based event comprises:
selecting at least one particular chemical profile from the number of chemical profiles; and
comparing the particular chemical profile to a plurality of reference chemical profiles to determine whether the particular chemical profile substantially matches any of the plurality of reference chemical profiles, wherein each of the plurality of reference chemical profiles is associated with a known cause.

13. The method of claim 12 further comprising:
determining whether the chemical-based event is reproducible within selected tolerances when the aircraft is made to have the flight configuration; and
linking the flight configuration of the aircraft to the chemical-based event in response to a determination that the chemical-based event is reproducible within the selected tolerances when the aircraft is made to have the operation configuration.

14. A chemical investigation system comprising:
a portable chemical profiling device that collects a number of samples of air at a number of locations inside a vehicle in response to a detection of a chemical-based event inside the vehicle and generates a number of chemical profiles for the number of samples on-site using the portable chemical profiling device to identify a probable location of the chemical-based event relative to the vehicle based on relative concentrations of the chemical profiles for the number of samples;
a database storing a plurality of reference chemical profiles associated with a plurality of known causes of chemical-based events in the vehicle; and
a cause identification system that identifies an operation configuration of the vehicle at a time at which the chemical-based event was detected, and identifies a probable cause of the chemical-based event using the number of chemical profiles, the probable location, and the operation configuration of the vehicle.

15. The chemical investigation system of claim 14, wherein the portable chemical profiling device is a portable gas chromatography-mass spectrometry device.

16. The chemical investigation system of claim 14, wherein the portable chemical profiling device comprises:
a sampling element that collects the number of samples of the air, wherein each of the number of samples collected has a volume sufficient to identify a number of chemical compounds in the each of the number of samples based on a corresponding chemical profile in the number of chemical profiles generated for the each of the number of samples.

17. The chemical investigation system of claim 14, wherein the cause identification system is configured to access the database using at least one of a wired communications link or a wireless communications link.

18. The method of claim 1, wherein the probable cause of the chemical-based event is a mechanical event caused by a change in the operation configuration, wherein the mechanical event is selected from the group consisting of an off-gassing of volatile organic compounds during the operation configuration, a leakage of battery cell fluid during the operation configuration, a problem with a valve that occurs during the operation configuration, a vehicle system being shut-off at the wrong time during the operation configuration, and a vehicle system being turned on at the wrong time during the operation configuration.

19. The method of claim 9, wherein the probable cause of the chemical-based event is a mechanical event caused by a change in the operation configuration, wherein the mechanical event is selected from the group consisting of an off-gassing of volatile organic compounds during the operation configuration, a leakage of battery cell fluid during the operation configuration, a problem with a valve that occurs during the operation configuration, a vehicle system being shut-off at the wrong time during the operation configuration, and a vehicle system being turned on at the wrong time during the operation configuration.

20. The chemical investigation system of claim 14, wherein the probable cause of the chemical-based event is a mechanical event caused by a change in the operation configuration, wherein the mechanical event is selected from the group consisting of an off-gassing of volatile organic compounds during the operation configuration, a leakage of battery cell fluid during the operation configuration, a problem with a valve that occurs during the operation configuration, a vehicle system being shut-off at the wrong time during the operation configuration, and a vehicle system being turned on at the wrong time during the operation configuration.

* * * * *